US007772411B2

(12) United States Patent
Goyvaerts et al.

(10) Patent No.: US 7,772,411 B2
(45) Date of Patent: Aug. 10, 2010

(54) PROCESS FOR THE PREPARATION OF (3R,3AS,6AR)-HEXAHYDROFURO [2,3-B] FURAN-3-YL (1S,2R)-3[[(4-AMINOPHENYL) SULFONYL] (ISOBUTYL) AMINO]-1-BENZYL-2-HYDROXYPROPYLCARBAMATE

(75) Inventors: Nicolaas Martha Felix Goyvaerts, Berlaar (BE); Piet Tom Bert Paul Wigerinck, Terhagen (BE); Hartmut Burghard Zinser, Schaffhausen (CH); Birgit M. Ebert, Schaffhausen (CH)

(73) Assignee: Tibotec Pharmaceuticals Ltd. (IE)

( * ) Notice: Subject to any disclaimer, the term of this patent is extended or adjusted under 35 U.S.C. 154(b) by 791 days.

(21) Appl. No.: 10/596,732

(22) PCT Filed: Dec. 23, 2004

(86) PCT No.: PCT/EP2004/053692

§ 371 (c)(1),
(2), (4) Date: Jun. 22, 2006

(87) PCT Pub. No.: WO2005/063770

PCT Pub. Date: Jul. 14, 2005

(65) Prior Publication Data

US 2007/0060642 A1 Mar. 15, 2007

Related U.S. Application Data

(60) Provisional application No. 60/568,183, filed on May 4, 2004.

(30) Foreign Application Priority Data

Dec. 23, 2003 (EP) .................................. 03104949

(51) Int. Cl.
C07D 493/04 (2006.01)
(52) U.S. Cl. .................................. 549/464
(58) Field of Classification Search .................. 549/464
See application file for complete search history.

(56) References Cited

U.S. PATENT DOCUMENTS 6,248,775 B1   6/2001   Vazquez et al.
6,455,738 B1   9/2002   Dubac et al.

FOREIGN PATENT DOCUMENTS

| EP | 0715618 B1 | 12/1998 |
| EP | 0754669 B1 | 10/2001 |
| EP | 0774453 B1 | 2/2002 |
| EP | 1081133 B1 | 3/2004 |
| EP | 0129856 B1 | 6/2004 |
| EP | 1215209 B1 | 8/2004 |
| EP | 1466898 A1 | 10/2004 |
| EP | 1067125 B1 | 7/2006 |
| WO | WO 94/04492 A1 | 3/1994 |
| WO | WO 94/05639 | 3/1994 |
| WO | WO 95/06030 | 3/1995 |
| WO | WO 96/22287 A1 | 7/1996 |
| WO | WO 96/28418 A1 | 9/1996 |
| WO | WO 96/28463 | 9/1996 |
| WO | WO 96/28464 | 9/1996 |
| WO | WO 96/28465 A1 | 9/1996 |
| WO | WO 97/18205 | 5/1997 |
| WO | WO 97/21685 A1 | 6/1997 |
| WO | WO 98/07685 A1 | 2/1998 |
| WO | WO 99/48885 A1 | 9/1999 |
| WO | WO 99/67417 A2 | 12/1999 |
| WO | WO 01/12599 A1 | 2/2001 |
| WO | WO 01/46120 A1 | 6/2001 |
| WO | WO 02/092595 A1 | 11/2002 |
| WO | WO 03/022853 A1 | 3/2003 |
| WO | WO 03/057665 A1 | 7/2003 |
| WO | WO 03/106461 A2 | 12/2003 |

OTHER PUBLICATIONS

Jain et al., "Polymorphism in Pharmacy" Indian Drugs ,1986, 23(6) 315-329.*
Vippagunta et al., "Crystalline Solid", Advanced Drug Delivery Reviews 48 (2001) 3-26.*
Guillory (in Brittain ed.), "Polymorphism, etc.," NY: Marcel Dekker, Inc., 1999, 1-2, 183-226.*
International Search Report, International Application No. PCT/EP2004/053692, Date of Mailing of International Search Report, May 2, 2005.
Bodanszky, M., *Principles of Peptide Synthesis*, $1^{st}$ and $2^{nd}$ revised edition, 1984 and 1993, Springer-Verlag, New York.
Cerfontain, Hans., *Mechanistic Aspects in Aromatic Sulfonation and Desulfonation*, 1968, Interscience Publishers, New York.
Cross L.C., et al., "Rules for The Nomenclature of Organic Chemistry, Section E: Sterochemistry.", *Pure & Appl. Chem.*, 1976, vol. 45, pp. 11-30.
Fieser et al., *Reagents for Organic Synthesis*, 1994, vol. 17, John Wiley & Sons.
Ghosh, A.K. et al., "Nonpeptidal P2 Ligands for HIV Protease Inhibitores: Structure-Based Design Synthesis and Biological Evaluation.", *Journal of Medicinal Chemistry*, 1996, vol. 39, pp. 3278-3290, American Chemical Society, Washington, US, XP002193358.

(Continued)

Primary Examiner—Patricia L Morris

(57) ABSTRACT

The present invention relates to a process for the preparation of (3R,3aS,6aR)-hexahydrofuro[2,3-b]furan-3-yl (1S,2R)-3-[[(4-aminophenyl)sulfonyl](isobutyl) amino]-1-benzyl-2-hydroxypropylcarbamate as well as intermediates for use in said process. More in particular the invention relates to processes for the preparation of (3R,3aS,6aR)-hexahydrofuro[2,3-b]furan-3-yl (1S,2R)-3-[[(4-aminophenyl)sulfonyl](isobutyl)amino]-1-benzyl-2-hydroxypropylcarbamate which make use of 4-amino-N-((2R,3S)-3-amino-2-hydroxy-4-phenylbutyl)-N-(isobutyl)benzene sulfonamide intermediate, and to processes amenable to industrial scaling up. (3R, 3aS,6aR)-hexahydrofuro[2,3-b]furan-3-yl (1S,2R)-3-[[(4-aminophenyl)sulfonyl](isobutyl)amino]-1-benzyl-2-hydroxypropylcarbamate is particularly useful as HIV protease inhibitors.

18 Claims, No Drawings

OTHER PUBLICATIONS

Ghosh, A.K. et al., "Potent HIV Protease Inhibitors Incorporating High-Affinity P2-ligands and (R)- Hydroxyethylamino)Sulfonamide Isostere.", *Bioorganic & Medicinal Chemistry Letters*, Mar. 17, 1998, vol. 8, No. 6, pp. 687-690, Oxford, GB, XP004136945.

Gilbert, Everett, E., *Sulfonation and Related Reactions*, 1977, Interscience Publishers, New York.

Greene T. W., et al., "*Protective Groups in Organic Synthesis*" $2^{nd}$ edition, T W Greene & P G M Wutz, 1991, Wiley Interscience.

Kim, B.M. et al., "Synthesis of a Chiral Aziridine Derivativeas a Versatile Intermediate for HIV Protease Inhibitors.", *Organic Letters*, 2001, vol. 3, No. 15, 2001, pp.2349-2351, XP0001179485.

March, J., "*Advanced Organic Chemistry*", $3^{rd}$ edition, 1985, pp. 1036-1039.

McManus, S.P. et al., "The Synthesis of Aminoalcohols From Epoxides and Amonia.", *Synthetic Communications*, 1973, vol. 3, No. 3, pp. 177-180.

Paquette, Leo A., *Encyclopedia of Reagents for Organic Synthesis*, 1995, John Wiley & Sons, New York, US.

Stewart, J.M. et al., *Solid Phase Peptide Synthesis*, $2^{nd}$ edition, 1984, W.H. Freeman and Company, San Franciso, CA.

Office Action dated Sep. 29, 2008 for corresponding European Application No. 04805020.7 - 2117/1725566.

* cited by examiner

PROCESS FOR THE PREPARATION OF (3R,3AS,6AR)-HEXAHYDROFURO [2,3-B] FURAN-3-YL (1S,2R)-3-[[(4-AMINOPHENYL) SULFONYL] (ISOBUTYL) AMINO]-1-BENZYL-2-HYDROXYPROPYLCARBAMATE

CROSS REFERENCE TO RELATED APPLICATIONS

This application is the national stage of PCT Application No. PCT/EP2004/053692, filed Dec. 23, 2004, which application claims priority from European Patent Application No. 03104949.7, filed 23 Dec. 2003 and U.S. provisional Patent Application No. 60/568,183, filed 4 May 2004, the entire disclosures of which are hereby incorporated in their entirely.

FIELD OF THE INVENTION

The present invention relates to a process for the preparation of (3R,3aS,6aR)-hexahydrofuro [2,3-b]furan-3-yl (1S, 2R)-3-[[(4-aminophenyl)sulfonyl](isobutyl) amino]-1-benzyl-2-hydroxypropylcarbamate as well as intermediates for use in said processes. More in particular the invention relates to processes for the preparation of (3R,3aS,6aR)-hexahydrofuro[2,3-b]furan-3-yl (1S,2R)-3-[[(4-aminophenyl)sulfonyl] (isobutyl)amino]-1-benzyl-2-hydroxypropylcarbamate which make use of 4-amino-N-[(2R,3S)-3-amino-2-hydroxy-4-phenylbutyl]-N-isobutylbenzene sulfonamide intermediate, and which are processes amenable to industrial scaling up.

BACKGROUND

The virus causing the acquired immunodeficiency syndrome (AIDS) is known by different names, including T-lymphocyte virus III (HTLV-III) or lymphadenopathy-associated virus LAV) or AIDS-related virus (ARV) or human immunodeficiency virus (HIV). Up until now, two distinct families have been identified, i.e. HIV-1 and HIV-2. Hereinafter, HIV will be used to generically denote these viruses.

One of the critical pathways in a retroviral life cycle is the processing of polyprotein precursors by retroviral protease. For instance, during the replication cycle of the HIV virus, gag and gag-pol gene transcription products are translated as proteins, which are subsequently processed by a virally encoded protease to yield viral enzymes and structural proteins of the virus core. Most commonly, the gag precursor proteins are processed into the core proteins and the pol precursor proteins are processed into the viral enzymes, e.g., reverse transcriptase and retroviral protease. Correct processing of the precursor proteins by the retroviral protease is necessary for the assembly of infectious virions, thus making the retroviral protease an attractive target for antiviral therapy. In particular for HIV treatment, the HIV protease is an attractive target.

Several protease inhibitors are on the market or are being developed. Hydroxyethylamino sulfonamide HIV protease inhibitors, for example 4-aminobenzene hydroxyethylamino sulfonamides, have been described to have favourable pharmacological and pharmacokinetic properties against wild-type and mutant HIV virus. Amprenavir is a commercially available exponent of this 4-aminobenzene hydroxyethylamino sulfonamide class of protease inhibitor. A process for the synthesis of amprenavir is described in WO99/48885 (Glaxo Group Ltd.).

4-aminobenzene hydroxyethylamino sulfonamides may also be prepared according to the procedures described in EP 715618, WO 99/67417, U.S. Pat. No. 6,248,775, and in Bioorganic and Chemistry Letters, Vol. 8, pp. 687-690, 1998, "Potent HIV protease inhibitors incorporating high-affinity P₂-ligands and (R)-(hydroxyethylamino) sulfonamide isostere", all of which are incorporated herein by reference. In particular, (3R,3aS,6aR)-hexahydrofuro[2,3-b]furan-3-yl (1S,2R)-3-[[(4-aminophenyl) sulfonyl](isobutyl)amino]-1-benzyl-2-hydroxypropylcarbamate, herein referred to as compound of formula (6), and methods for its preparation may be found disclosed in WO99/67417 (USA, The Secretary, Dpt. of Health and Human Services), and in PCT/EP03/50176 (Tibotec N.V.).

WO03/057665 (Ajinomoto KK) relates to a process for producing crystals of benzenesulfonamide derivatives. In particular, it provides a crystallization for (2R,3S) -N-(3-amino-2-hydroxy-4-phenylbutyl)-N-isobutyl-4-amino-benzensulfonamide, which is an intermediate of interest for the preparation of (3R,3aS,6aR)-hexahydrofuro [2,3-b]furan-3-yl (1S,2R)-3-[[(4-aminophenyl)sulfonyl](isobutyl)amino]-1-benzyl-2-hydroxypropylcarbamate. This intermediate of interest is obtained according to the disclosure by departing from a (2S,3S)-3-benzyloxycarbonylamino-1,2-epoxy-4-phenylbutane, to which isobutylamite is reacted, followed by coupling of p-nitro-benzenesulfonylchloride to yield (2R, 3S)-N-(3-benzyloxycarbonylamino-2-hydroxy-4-phenylbutyl)-N-isobutyl-4-nitrobenzenesulfonamide, which is simultaneously reduced and deprotected to obtain the intermediate of interest. In particular, the route employs a benzyloxycarbonyl (Cbz or Z) as the amino protecting group of the core molecule. It is observed that the simultaneous reduction of the nitro moiety and Cbz deprotection in (2R,3S)-N-(3-benzyloxycarbonylamino-2-hydroxy-4-phenylbutyl)-N-isobutyl-4-nitrobenzenesulfonamide results in a highly exothermic reaction. Exothermic reactions, if possible, should be avoided or limited to its minimum extent, as they are more difficult for controlling reaction temperatures, i.e. when the reaction temperature would be too low, the reaction rate is small and a long time is required; when the reaction temperature would be too high, the reaction rate is too large and insufficient mixing occurs, inviting nonuniform reaction, deterioration (burning) of the product formed, or unwanted side reactions may take place with the result that product selectivity is decreased. On the other hand, it is also observed that the catalytic reduction disclosed in WO03/057665 does not include an acid treatment. In the absence of an acid treatment, it is expected that the catalyst employed during reduction and Cbz deprotection will be poisoned with the sulfur from p-nitrobenzenesulfonyl-chloride. A poisoned catalyst will inevitably result into the appearance of side-products thus decreasing product selectivity.

In order for a chemical route to be suitable for industrial scale, it should produce compounds in acceptable yields and purity while being easy and simple to carry out, as well as cost effective. As such, there has been found a new process for the synthesis of compound of formula (6) which is amenable for industrial scale.

(6)

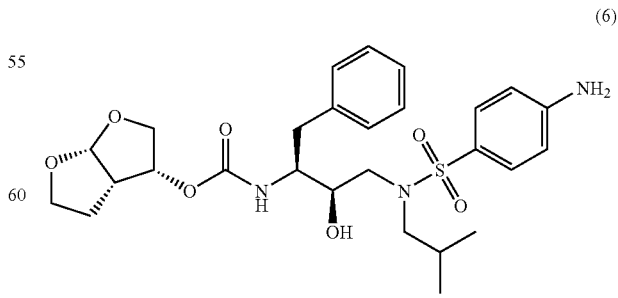

In particular, the present invention provides a convenient process for the production of compound of formula (6) and intermediates, addition salts, polymorphic and/or pseudopolymorphic forms thereof at industrial scales. More in particular, the present invention encompasses a suitable route for the synthesis of compound of formula (6) which further benefits from an improved and cost-effective crystallization of (2R,3S)-N-(3-amino-2-hydroxy-4-phenylbutyl)-N-isobutyl-4-amino-benzenesulfonamide with acceptable purities and yields. Even more in particular, the present invention presents separate reduction and deprotection reactions encompassing an acid treatment, all resulting in a more controllable, selective and cost-effective process.

In one embodiment, the present invention provides an improved crystallization employing pH and concentration controls in defined ranges, while the crystallization by WO03/057665 only makes mention of heating the solution in polar solvent in order to improve the yield, or heating the solution (30-80° C.) in order to dissolve the crystals present in the polar solvent solution in order to improve purification.

The present invention has the further advantage of using commercially available starting material, such as a 1-oxiranyl-2-phenyl-ethyl-carbamic acid tert-butyl ester. Further, the precursor of compound of formula (6), i.e. (2R,3S)-N-(3-amino-2-hydroxy-4-phenylbutyl)-N-isobutyl-4-amino-benzenesulfonamide or compound of formula (5), may be produced as a one-pot procedure which results in an efficient utilization of the reactor and the omission of intermediate purification steps. The reagents further used in said process are safe and available in bulk. Furthermore, each step of said method is performed at controllable conditions and provides with the desired compound in optional yields. Moreover, each step of said process is performed stereoselectively, which allows the synthesis of pure stereoisomeric forms of the desired compounds.

Other objects and advantages of the present invention will become apparent from the following detailed description taken in conjunction with the accompanying examples.

EP0754669 (Kaneka Corporation) describes processes for producing alpha-halo ketones, alpha-halohydrins and epoxides; EP1029856 (Kaneka Corp.) discloses a process for the preparation of (2R,3S)-3-amino-1,2-oxirane; and EP1067125 also by Kaneka Corporation relates to a process for the preparation of threo-1,2-epoxy-3-amino-4-phenylbutane. EP774453 (Ajinomoto Co., Inc.) describes a process for producing 3-amino-2-oxo-1-halogenopropane derivatives. In WO01/12599 (Samchully Pharm Co. Ltd.) there is described new ethylaziridine derivatives and their preparation methods. WO01/46120 (Aerojet Pine Chemicals LLC) discloses an improved preparation of 2S,3S-N-isobutyl-N-(2-hydroxy-3-amino-4-phenylbutyl)-p-nitrobenzenesulfonylamide hydrochloride and other derivatives of 2-hydroxy-1,3-diamines. In WO96/28418 (G. D. Searle & Co., Inc.) there are disclosed sulfonylalkanoylamino hydroxyethylamino sulfonamide retroviral protease inhibitors. WO94/04492 (G. D. Searle & Co., Inc.) discloses alpha- and beta-amino acid hydroxyethylamino sulfonamides useful as retroviral protease inhibitors. WO97/21685 (Abbott) discloses the preparation of peptide analogues as retroviral protease inhibitors. WO94/05639 (Vertex Pharmaceuticals) describes sulfonamide inhibitors of HIV-1 aspartyl protease.

DETAILED DESCRIPTION OF THE INVENTION

The present invention relates to a process for the preparation of compound of formula (6), addition salts, polymorphic and/or pseudopolymorphic forms thereof;

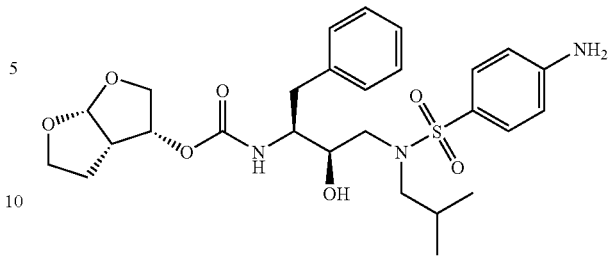

(6)

which comprises:
(i) introducing an isobutylamino group in compound of formula (1)

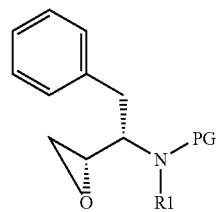

(1)

wherein
PG represents an amino-protecting group;
$R_1$ is hydrogen or $C_{1-6}$alkyl;
(ii) introducing a p-nitrophenylsulfonyl group in the resultant compound of step (i);
(iii) reducing the nitro moiety of the resultant compound of step (ii);
(iv) deprotecting the resultant compound of step (iii); and
(v) coupling the resultant compound of step (iv) with a (3R,3aS,6aR)-hexahydrofuro[2,3-b]furan-3-yl derivate, to form compound of formula (6).

In one embodiment, the present invention relates to a process for preparing compound of formula (6), characterized in that said process comprises the steps of: introducing an isobutylamino group in compound of formula (1');

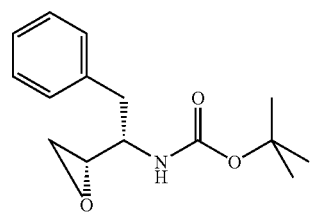

(1')

to obtain compound of formula (2');

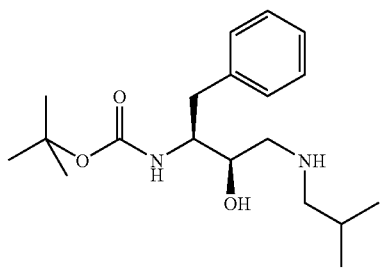

(2')

introducing a p-nitrophenylsulfonyl group into compound of formula (2') to obtain compound of formula (3');

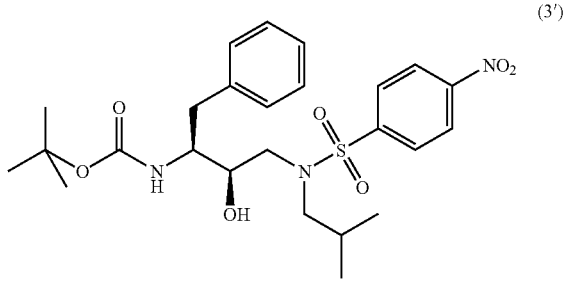

(3')

reducing the nitro moiety of compound of formula (3') to obtain compound of formula (4');

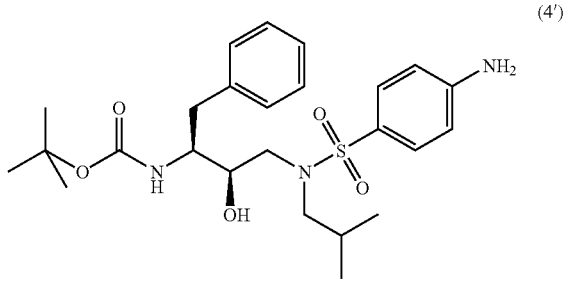

(4')

deprotecting compound of formula (4') to obtain compound of formula (5);

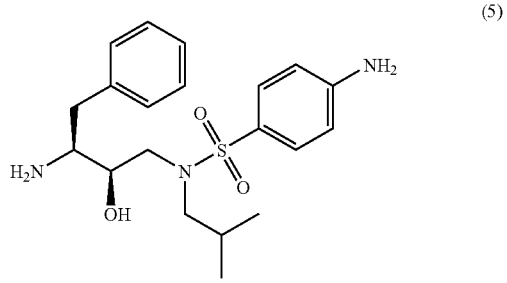

(5)

coupling compound of formula (5) with (3R,3aS,6aR)-hexahydrofuro[2,3-b]furan-3-yl derivate to obtain compound of formula (6).

The present invention thus involves processes for the preparation of compound of formula (6), addition salts, polymorphic and/or pseudopolymorphic forms thereof, through the intermediate of formula (5)

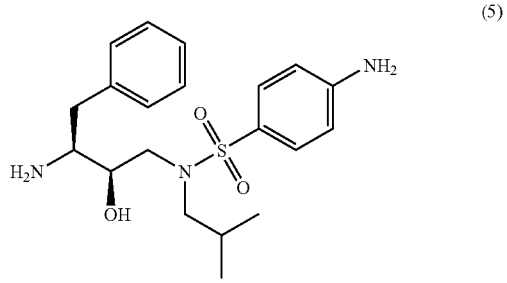

(5)

Preferably, compound of formula (5) is crystallized as a freebase. Alternatively, compound of formula (5) is crystallized as a salt with strong acids such as hydrochloric acid, hydrobromic acid, methanesulfonic acid, sulfuric acid, oxalic acid, citric acid, and the like. Crystallization of compound of formula (5) improves its purity and yield, both beneficial factors for the production of compound of formula (6). Alternatively, compound of formula (5) may be crystallized as a polymorphic and/or pseudopolymorphic form thereof.

Preferably, compound of formula (6) is crystallized as a pseudopolymorphic form, preferably as an alcoholate, more preferably as an ethanolate.

Compound of Formula (1)
Compound of formula (1) is

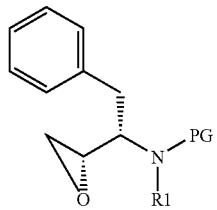

(1)

wherein
PG represents an amino-protecting group;
$R_1$ is hydrogen or $C_{1-6}$alkyl.

The term "amino-protecting group" as used herein refers to one or more selectively removable substituents on the amino group commonly employed to block or protect the amino functionality against undesirable side reactions during synthetic procedures and includes all conventional amino protecting groups. Examples of amino-protecting groups include the urethane blocking groups, such as t-butoxy-carbonyl ("Boc"), 2-(4-biphenylyl)propyl(2)oxycarbonyl ("Bpoc"), 2-phenylpropyl(2)oxycarbonyl ("Poc"), 2-(4-xenyl)isopropoxycarbonyl, isopropoxycarbonyl, 1,1-diphenylethyl(1)-oxycarbonyl, 1,1-diphenylpropyl(1)oxycarbonyl, 2-(3,5-dimethoxyphenyl)propyl(2)-oxycarbonyl ("Ddz"), 2-(p-5-toluyl)propyl(2)oxycarbonyl, 1-methylcyclopentanyloxycarbonyl, cyclohexanyloxycarbonyl, 1-methylcyclohexanyloxycarbonyl, 2-methylcyclohexanyloxycarbonyl, ethoxycarbonyl, 2-(4-toluylsulfonyl)ethoxycarbonyl, 2-(methylsulfonyl)-ethoxycarbonyl, 2-(triphenylphosphino)-ethoxycarbonyl, 9-fluoroenylmethoxycarbonyl ("Fmoc"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, tribromoethoxycarbonyl, 2-ethynyl(2)propoxycarbonyl, cyclopropylmethoxycarbonyl, isobornyloxycarbonyl, 1-piperidyloxycarbonyl, benzyloxycarbonyl ("Z" or "Cbz"), 4-phenylbenzyloxycarbonyl, 2-methylbenzyloxy-carbonyl, α-2,4,5,-tetramethyl-benzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, dichlorobenzyloxycarbonyl, 4-bromobenzyloxycarbonyl, ortho-bromobenzyloxycarbonyl, 3-bromobenzyloxycarbonyl, 4-nitrobenzyloxycarbonyl, 4-cyanobenzyloxycarbonyl, 4-(decyloxy)benzyloxycarbonyl, and the like; the benzoylmethylsulfonyl group, dithiasuccinoyl ("Dts") group, the 2-(nitro)phenylsulfenyl group ("Nps"), the diphenylphosphine oxide group, and the like. The species of amino-protecting group employed is usually not critical so long as the derivatized amino group is stable to the conditions of the subsequent reactions and can be removed at the appropriate point without disrupting the remainder of the compound.

Additional examples of amino protecting groups include phenylacetyl, formyl ("For"), trityl (Trt), acetyl, tifluoroacetyl (TFA), trichloroacetyl, dichloroacetyl, chloroacetyl, bromoacetyl, iodoacetyl, benzoyl, tert-amyloxycarbonyl, tert-butoxycarbonyl, 3,4-dimethoxybenzyloxycarbonyl, 4-(phenylazo)benyloxycarbonyl, 2-furfuryloxycarbonyl, diphenylmethoxycarbonyl, 1,1-dimethylpropoxycarbonyl, phthalyl or phthalimido, succinyl, alanyl, leucyl, and 8-quinolyloxycarbonyl, benzyl, diphenylmethyl, 2-nitrophenylthio, 2,4-dinitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthylmethylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclohexylidene, diphenylphosphoryl, dibenzylphosphoryl, 5-methyl-2-oxo-2H-1,3-dioxol-4-yl-methyl, trimethylsilyl triethylsilyl, triphenylsilyl, 2-(p-biphenyl)-1-methylethoxycarbonyl, diisopropylmethoxycarbonyl, cyclopentyloxycarbonyl, adamantyloxycarbonal, triphenylmethyl, trimethylsilane, phenylthiocarbonyl, para-nitrobenzylcarbonyl.

Other amino protecting groups include 2,7-di-t-butyl-[9-(10,10-dioxo-10,10,10,10-tetrahydrothio-xanthyl)]methyloxycarbonyl; 2-trimethylsilylethyloxycarbonyl; 2-phenylethyloxycarbonyl; 1,1-dimethyl-2,2-dibromoethyloxycarbonyl; 1-methyl-1-(4-biphenylyl)ethyloxycarbonyl; p-nitrobenzyloycarbonyl; 2-(p-toluenesulfonyl)-ethyloxycarbonyl; m-chloro-p-acyloxybenzyloxycarbonyl; 5-benzyisoxazolylmethyloxycarbonyl; p-(dihydroxyboryl)benzyloxycarbonyl; m-nitrophenyloxycarbonyl; o-nitrobenzyloxycarbonyl; 3,5-dimethoxybenzyoxycarbonyl; 3,4-dimethoxy-6-nitrobenzyloxycarbonyl; N'-p-tolunesulfonylaminocarbonyl; t-amyloxycarbonyl; p-decyloxybenzyloxycarbonyl; 2,2-dimethoxycarbonylvinyloxycarbonyl; di(2-pyridyl)methyloxycarbonyl; 2-furanylmethyloxycarbonyl; dithiasuccinimide; 2,5-dimethylpyrrole; 5-dibenzylsuberyl; and, methanesulfonamide. Preferred amino-protecting group is Boc.

Further examples of amino-protecting groups are well known in organic synthesis and the peptide art and are described by, for example T. W. Greene and P. G. M. Wuts, *Protective Groups in Organic Synthesis*, 2nd ed., John Wiley and Sons, New York, Chapter 7, 1991; M. Bodanzsky, *Principles of Peptide Synthesis*, 1st and 2nd revised ed., Springer-Verlag, New York, 1984 and 1993; Stewart and Young, *Solid Phase Peptide Synthesis*, 2nd ed., Pierce Chemical Co, Rockford, Ill. 1984; L. Fieser and M. Fieser, *Fieser and Fieser's Reagents for Organic Synthesis*, John Wiley and Sons (1994); L. Paquette, ed. *Encyclopedia of Reagents for Organic Synthesis*, John Wiley and Sons (1995). Suitable amino protecting groups are also given in e.g. WO98/07685.

The term "$C_{1-6}$alkyl" as a group or part of a group defines straight and branched chained saturated hydrocarbon radicals having from 1 to 6 carbon atoms such as methyl, ethyl, isopropyl, butyl, pentyl, hexyl, 2-methylbutyl, 3-methylpentyl and the like.

Preferably compound of formula (1) is compound of formula (1') as shown below wherein PG is a tert-butyloxycarbonyl or "Boc", and $R_1$ is hydrogen. Compounds of formula (1) and (1') are commercially available and may be prepared in several ways available in the literature, for example as described in WO95/06030 (Searle & Co.), as described by Kaneka Corporation in EP0754669 EP1029856 and EP1067125, and as disclosed by Ajinomoto KK in EP1081133 and EP1215209.

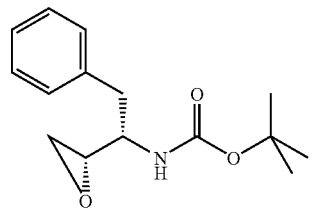

Compound of Formula (2)

Compound of formula (1) is subjected to an amination on the epoxide to render compound of formula (2).

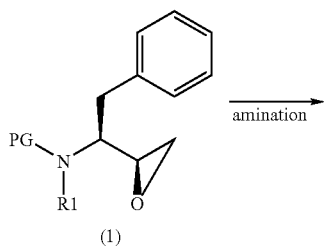

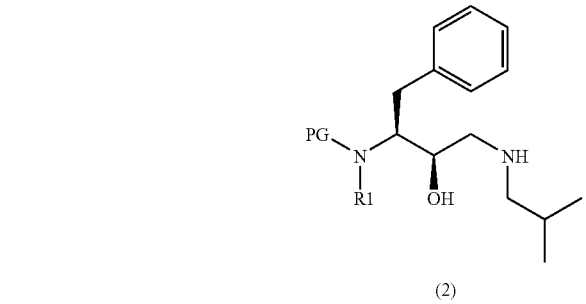

The term "amination" as used herein refers to a process in which a primary amine, isobutylamine, is introduced into the organic molecule of formula (1). Amination of compound of formula (1) may be accomplished in several ways available in the literature, for example as described in WO95/06030, which is incorporated herein by reference.

In a preferred embodiment, compound of formula (1') is reacted with isobutylamine to yield compound of formula (2').

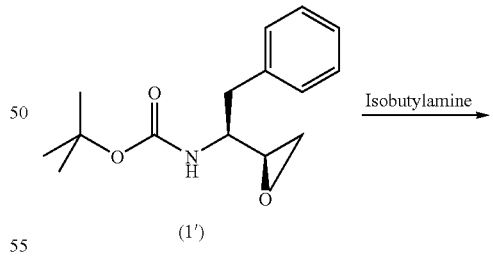

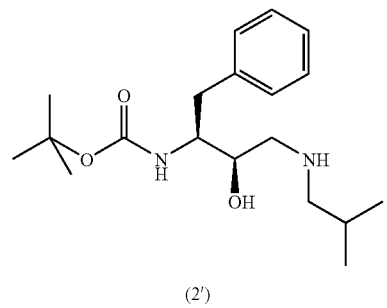

Amination of epoxides is described for instance in March, Advanced Organic Chemistry 368-69 (3rd Ed. 1985) and McManus et al, 3 Synth. Comm. 177 (1973), which are incorporated herein by reference. Suitably, compounds of formula (2) and (2') may be prepared according to the procedure described in WO97/18205.

The amination agent, isobutylamine, may function as well as a solvent, in which case, an excess of isobutylamine will be added. In other embodiments, the amination process is performed in the presence of one or more solvents other than isobutylamine. In a preferred embodiment, said solvents are used in the work-up of compounds of formula (2) and (2').

Suitable solvents include protic, non-protic and dipolar aprotic organic solvents such as, for example, those wherein the solvent is an alcohol, such as methanol, ethanol, isopropanol, n-butanol, t-butanol, and the like; ketones such as acetone; ethers such as diethyl ether, tetrahydrofuran, dioxane and the like; esters such as ethyl acetate, aminos such as triethylamine; amides such as N,N-dimethylformamide, or dimethylacetamide; chlorinated solvents such as dichloromethane and other solvents such as toluene, dimethyl sulfoxide, acetonitrile, and mixtures thereof. A preferred solvent is toluene.

Conveniently the reaction can be conducted over a wide range of temperatures, e.g., from about −20° C. to about 200° C., but is preferably, although not necessarily, conducted at a temperature at which the solvent refluxes, i.e. between 40° C. and 100° C., more preferably between 60° C. and 90° C.

Suitably the ratios of equivalents between the compound of formula (1) and the amination agent may range from 1:1 to 1:99, respectively. Preferably, the ratio of equivalents between the compound of formula (2) and the amination agent is from 1:5 to 1:20, more preferably the ratio is from 1:10 to 1:15.

In an embodiment of the invention, the amination reaction is carried out in the presence of about 15 equivalents of isobutylamine, using toluene as solvent, and heating to reflux at about 79° C.

Compounds of Formula (3)

Compound of formula (3) is prepared by introducing the sulfonyl moiety, p-nitrobenzene-$SO_2$, into the intermediate of formula (2).

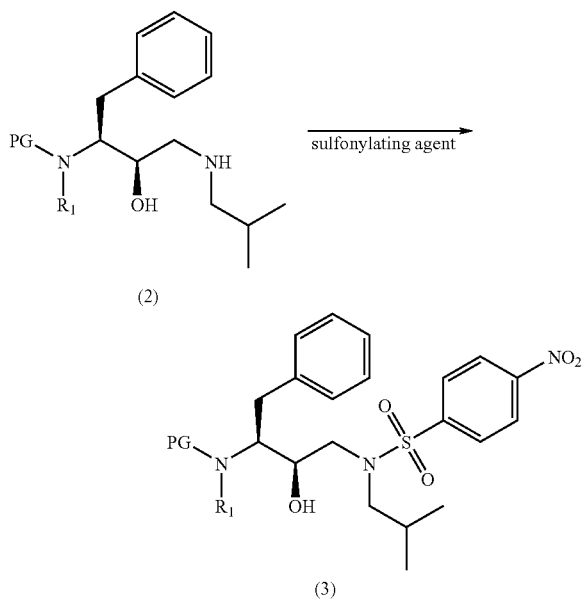

(2)

(3)

Thus, in a preferred embodiment compound of formula (3') will be prepared by sulfonylating compound of formula (2').

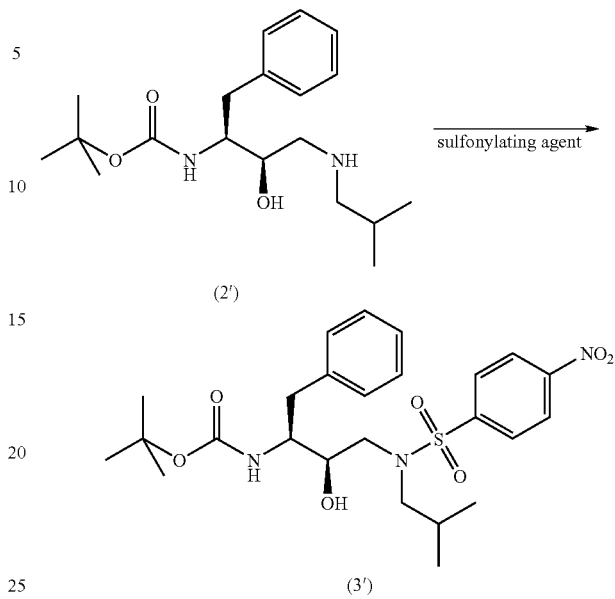

(2')

(3')

As such, compounds of formula (2) and (2') will react with a sulfonylating agent to transform into compounds of formula (3) and (3').

The term "sulfonylation" as used herein refers to a process in which p-nitrobenzene-sulfonyl moeity is introduced into the organic molecule of formulas (2) and (2'). The term "sulfonation" as used herein refers to a process in which a sulfonylating agent is prepared. The term "sulfonylating agent" is referred to p-nitrobenzene-sulfonyl derivatives, such as p-nitrobenzenesulfonyl haloderivatives.

The sulfonylating agents, and in particular p-nitrobenzenesulfonyl haloderivatives, can be prepared by the oxidation of thiols to sulfonyl chlorides using chlorine in the presence of water under carefully controlled conditions. Additionally, sulfonic acids may be converted to sulfonyl halides using reagents such as $PCl_5$, and also to anhydrides using suitable dehydrating reagents. The sulfonic acids may in turn be prepared using procedures well known in the art. Such sulfonic acids are also commercially available. Sulfonylating agents may as well be prepared by the sulfonation procedures described in "Sulfonation and Related Reactions", by E. E. Gilbert, R. E. Krieger Publishing Co. Huntington, N.Y. (1977), "Mechanistic Aspects of Aromatic Sulfonation and Desulfonation", by H. Cerfontain, Interscience Publishers, NY (1968), and in U.S. Pat. No. 6,455,738, "Process for the sulfonation of an aromatic compound", all incorporated herein by reference.

The treatment of compounds of formula (2) and (2') with the sulfonylating agent can be carried out in the presence of a solvent under heating, approximately between 25° to 250° C., preferably between 70° and 100° C. and agitation. After the sulfonylation, any remaining sulfonylating agent or salts are preferably, although not necessarily, removed from the reaction mixture. This removal can be accomplished by repeated washing with water, change of pH, separation of organic and aqueous phases, ultrafiltration, reverse osmosis, centrifugation, and/or filtration or the like.

The compounds having formula (3) and (3') are prepared by reacting a sulfonylating agent with intermediates of formula (2) and (2') in suitable solvents under alkaline conditions. Suitable alkaline conditions include conventional non-nucleophilic inorganic or organic bases and/or acid scavengers. Conventional non-nucleophilic inorganic or organic bases include, for example, hydrides, hydroxides, amides, alcoholates, acetates, carbonates, or hydrogen carbonates of alkaline earth metals or alkali metal hydrides such as, for example, sodium hydride, potassium hydride or calcium hydride, and metal amides, such as sodium amide, potassium amide, lithium diisopropylamide or potassium hexamethyldisilazide, and metal alkanes such as sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, sodium bicarbonate, potassium carbonate, potassium bicarbonate, cesium carbonate, potassium hydrogen carbonate, sodium hydrogen carbonate, or ammonium carbonate, and also basic organic nitrogen compounds such as, trialkylamines, like trimethylamine, triethylamine, tributylamine, N,N-dimethylaniline, N,N-dimethyl-benzylamine, N,N-diisopropylethylamine, pyridine, 1,4-diazabicyclo[2.2.2]-octane (DABCO), 1,5-diazabicyclo[4.3.0]-non-5-ene (DBN), or 1,8-diazabicyclo[5.4.0]-undec-7-ene (DBU), or an excess of an appropriate piperidine compound may be used. Preferably triethylamine is used.

Suitable solvents have been illustrated in the preparation of formulas (2) and (2') above, being inert solvents preferred, such as for example toluene, ethylacetate, methylene chloride, dichloromethane, and tetrahydrofuran.

Conveniently, the ratios of equivalents, calculated from compounds of formula (1) or (1'), and the sulfonylating agent range from 1:1 to 1:3, respectively. Preferably, the ratio of equivalents between the compounds of formula (1) or (1') and the sulfonylating agent is from 1:1 to 1:2, more preferably the ratio is around 1:1.15.

Compounds of Formula (4)

Compounds of formula (4) and (4') are obtained by reducing the nitro moiety of intermediates of formula (3) and (3') respectively with a reducing agent, optionally under a hydrogen atmosphere.

diborane, sodium borohydride, lithium borohydride, sodium borohydride-LiCl, aluminum lithium hydride, or diisobutylaluminium hydride; metals such as iron, zinc, tin and the like; and transition metals such as palladium-carbon, platinum oxide, Raney-nickel, rhodium, ruthenium and the like. When catalytic redaction is applied, ammonium formate, sodium dihydrogenphosphate, hydrazine may be used as the hydrogen source.

Solvents suitable for the reduction of the nitro moiety may be selected from water, alcohols, such as methanol, ethanol, isopropanol, tert-butyl alcohol, esters such as ethyl acetate, amides such as dimethylformamide, acetic acid, dichloromethane, toluene, xylene, benzene, pentane, hexane, heptane, petrol ether, 1,4-thioxane, diethyl ether, diisopropyl ether, tetrahydrofuran, 1,4-dioxane, 1,2-dimethoxiethane, dimethyl sulfoxide, or mixtures thereof. In general any solvent susceptible to being used in a chemical reduction process may be used.

Said reduction step can be carried out at temperatures that range between −78° C. and 55° C., preferably between −10° and 50° C., the preferred temperatures lying between 0° C. and 50° C., more preferably between 5° C. and 30° C. The reaction time may range from 30 minutes to 2 days, more suitably from 1 hour up to 24 hours. According to a preferred embodiment, the reduction step is performed using palladium on charcoal suspended in methanol in another preferred embodiment, an additional amount of charcoal may be employed.

The ratios of equivalents between compounds of formula (3) or (3'), and hydrogen range from 1:1 to 1:10, respectively. Preferably, the ratio of equivalents between the compounds of formula (3) or (3') and the hydrogen is from 1:1 to 1:5, more preferably the ratio is around 1:3.

Compounds of Formula (5)

Compound of formula (5) is obtained by deprotecting the intermediates of formula (4) and (4') under conventional acidic conditions. Alternatively basic conditions may be applied.

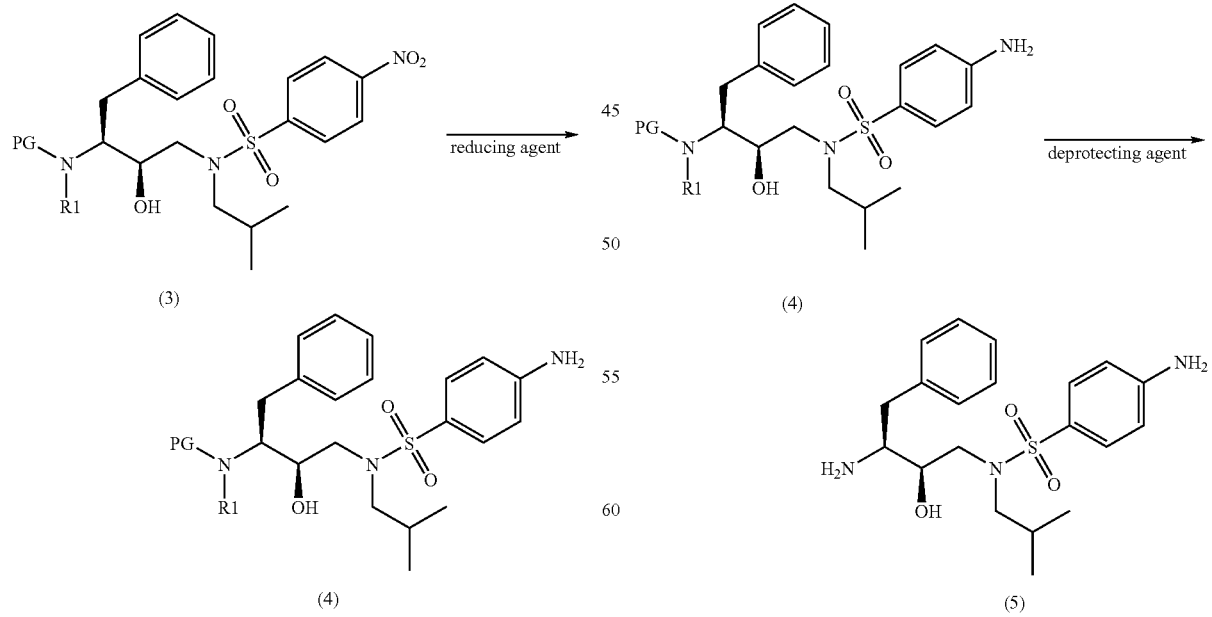

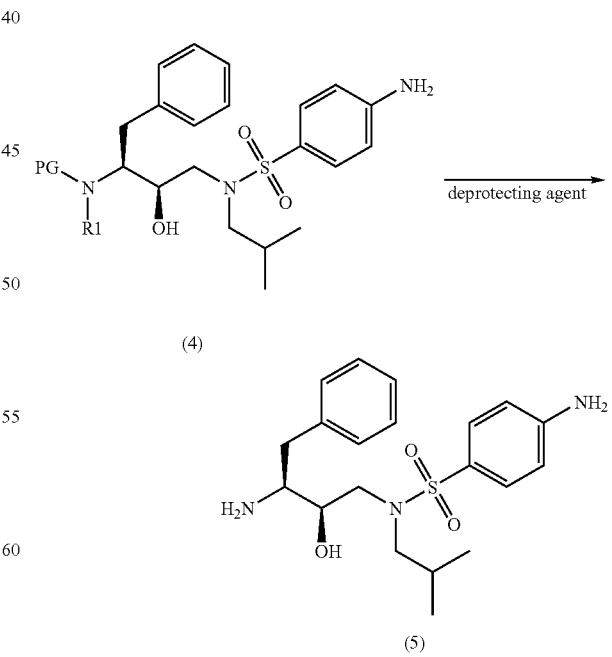

Reducing agents suitable for reduction of the nitro moiety are metallic reducing reagents such as borane complexes, Removal of the amino-protecting-group can be achieved using conditions which will not affect the remaining portion of the molecule. These methods are well known in the art and include acid hydrolysis, hydrogenolysis and the like, thus using commonly known acids in suitable solvents.

Examples of acids employed in the removal of the amino protecting group include inorganic acids such as hydrogen chloride, nitric acid, hydrochloric acid, sulfuric acid and phosphoric acid, organic acids such as acetic acid, trifluoroacetic acid methanesulfonic acid and p-toluenesulfonic acid; Lewis acids such as boron trifluoride; acidic cationic ion-exchange resins such as Dowex 50W™. Of these acids, inorganic acids and organic acids are preferred. Hydrochloric acid, sulfuric acid, phosphoric acid and trifluoroacetic acid are more preferred, and hydrochloric acid is most preferred.

The solvent employed during the deprotection of intermediates of formula (4) and (4') is not particularly limited provided that it has no adverse effect on the reaction and dissolves the starting materials to at least some extent. Suitable solvents are aliphatic hydrocarbons such as hexane, heptane and petroleum ether; aromatic hydrocarbons such as benzene, toluene, xylene and mesitylene; halogenated hydrocarbons such as methylene chloride, chloroform, carbon tetrachloride and dichloroethane; ethers such as diethyl ether, terahydrofuran, 1,4-dioxane and 1,2-dimethoxyethane; alcohols such as methanol, ethanol, propanol, isopropanol and butanol; esters such as methyl acetate, ethyl acetate, methyl propionate and ethyl propionate; nitrites such as aectonitrile; amides such as N,N-dimethylformamide and N,N-dimethylacetamide; sulfoxides such as dimethyl sulfoxide and mixtures thereof. Aromatic hydrocarbons, alcohols and esters are preferred. Alcohols and water are more preferred, and water, isopropanol, ethanol and methanol are particularly preferred. Mixtures of methanol, water, and isopropanol or ethanol, and mixtures of ethanol and water are also preferred.

The reaction temperature employed depends upon various factors such as the nature of the starting materials, solvents and acids. However it is usually between –20° C. and 150° C., and is preferably between 30° C. and 100° C., even more preferably at a temperature of reflux. The reaction time employed depends on the reaction temperature and the like. It is typically from 5 minutes to 72 hours, and preferably from 15 minutes to 4 hours.

Examples of reagents and methods for deprotecting amines from amino protecting groups can additionally be found in *Protective Groups in Organic Synthesis* by Theodora W. Greene, New York, John Wiley and Sons, Inc., 1981, incorporated herein by reference.

As those skilled in the art will recognize, the choice of amino protecting group employed in a previous step of the process will dictate the reagents and procedures used in removing said amino protecting group.

The ratios of equivalents between the compounds of formula (3) or (3') and the acid in solvent may range from 1:2 to 1:50, respectively. Preferably, the ratio of equivalents between the compounds of formula (3) or (3') and the acid is from 1:2 to 1:8, more preferably the ratio is around 1:2.

In a preferred embodiment of the present invention, compound of formula (5) is crystallized. Crystallization of compound of formula (5) is performed by dissolving compound of formula (5) in a solvent system, adjusting the pH of the solution and adjusting the concentration of the compound of formula (5). Alternatively, seed crystals of compound of formula (5) may be added.

The solvent system used in the crystallization may comprise one or more water-miscible solvents and water, or alternatively, the solvent system comprises one or more water-immiscible solvents and water.

Examples of water-miscible solvents encompass C1-C4 alcohols such as methanol, ethanol n-propanol, isopropanol, n-butanol, isobutanol; cyclic ethers such as tetrahydrofuran or dioxane; amides such as dimethylformamide, dimethylacetamide, N-methylpyrrolidone; dimethylsulfoxide, acetonitrile; a mixture of the abovementioned solvents with one another or a mixture with water, or water itself.

Examples of water-immiscible solvents are hydrocarbons such as pentane, hexane, cyclohexane, methylcyclohexane, heptane, toluene, xylene; C4-C8 esters such as methyl formate, ethyl formate, methyl acetate, ethyl acetate; C4-C8 ethers such as diethyl ether, tert-butyl methyl ether, isopropyl ether; chlorinated solvents such as methylene chloride, dichloromethane, chloroform, dichloroethane, chlorobenzene; or a binary or multiple mixture thereof. When such water-immiscible solvents are used, compound of formula (5) will be isolated by separation of the organic and aqueous phases.

Adjustment of concentration of compound of formula (5) may be accomplished by the addition of water or other suitable solvents, or by evaporation, distillation of the solvent or any other equivalent concentrating techniques. In a preferable crystallization, compound of formula (5) is kept at a concentration between 0.1% and 40% (w/w), preferably between 1% and 30%, more preferably between 2% and 20%, even more preferably between 4% and 15% w/w.

Monitoring or in-process control of the values of concentration of compound of formula (5) in solution may be performed by any method known to the skilled in the art, such as for example, by HPLC chromatography, measurement of density, titration, and the like.

Preferably the solvent used during crystallization of compound of formula (5) is the same as the solvent used during deprotection of intermediates of formula (4) or (4'). Alternatively, when more than one solvent is used, one or more of the solvents used during crystallization of compound of formula (5), are the same as one or more of the solvents used during deprotection of intermediates of formula (4) or (4').

Adjustment of the pH of the solution containing compound of formula (5) may be accomplished by the addition of basic compounds such as sodium hydroxide, sodium carbonate, potassium hydroxide, lithium hydroxide, ammonia, hydrazine, calcium hydroxide, methylamine, ethylamine, aniline, ethylenediamine, triethylamine, tetraethyl ammonium hydroxide, a C2-C18 amino, a C4-C18 ammonium hydroxide, sodium methoxide, potassium methoxide, a C1-C4 organic base, any of the bases listed above, and mixtures thereof. pH of the solution containing compound of formula (5) will be maintained in the basic range, preferably at a pH higher than 7, more preferably at a pH higher than 8, and even more preferably at a pH higher than 9.

In one embodiment, after addition of the base the suspension is further stirred during 1 hour to 48 hours, preferably during 1 to 10 hours, more preferably during 1 to 5 hours.

Working temperatures employed during precipitation of compound of formula (5) may range between –20° and 50° C. Preferably, working temperatures during precipitation may range between –15° C. to 10° C., even more preferably between –10° C. and 10° C., most preferably around 5° C. In another embodiment, compound of formula (5) is collected by centrifugation and dried in vacuum at around 65° C.

A preferred crystallized compound of formula (5) is the free base. Alternatively, other suitable compounds are those crystallized compounds of formula (5) in a salt form, wherein the salt is selected from hydrochloride, hydrobromide, trifluoroacetate, fumarate, chloroacetate and methanesulfonate, and the like.

Intermediates of formula (5) are also active inhibitors of retrovirus proteases.

(3R,3aS,6aR)-hexahydrofuro[2,3-b]furan-3-yl derivate (3R,3aS,6aR)-hexahydrofuro[2,3-b]furan-3-ol and precursors thereof, may be synthetised as described in WO 03/022853. (3R,3aS,6aR)-hexahydrofuro[2,3-b]furan-3-ol and precursors thereof are suitably activated with coupling agents to generate a (3R,3aS,6aR)-hexahydrofuro[2,3-b]furan-3-yl derivate which may undergo carbamoylation with compound of formula (5). Activation of (3R,3aS,6aR)-hexahydrofuro[2,3-b]furan-3-ol and precursors thereof with the coupling agent preferably occurs before the coupling with compound of formula (5). Said activation of (3R,3aS,6aR)-hexahydrofuro[2,3-b]furan-3-ol and precursors thereof and their coupling to compound of formula (5) has the additional advantage to be a one-pot procedure, since isolation of the activated intermediate is not necessary.

Precursors of (3R,3aS,6aR)-hexahydrofuro[2,3-b]furan-3-ol are those compounds where the oxygen of the alcohol function is protected with O-protecting groups, such as t-butyl ether ("Boc"), acetates, benzyl groups, benzyl ethers, allyls, silyl protecting groups such as tert-butyldimethylsilyl (TBS), trimethlysilylethoxymethyl (SEM), alkoxyalkyl groups such as methoxyethoxymethyl (MEM), methoxymethyl (MOM), tetrahydropyranyl (THP), tetrahydropyranyl (THE), and the like. Where precursors of (3R,3aS,6aR)-hexahydrofuro[2,3-b]furan-3-ol are employed, deprotection may be accomplished prior to the coupling or in situ. Removal of the alcohol protecting groups may be achieved in acidic or basic conditions, being acidic conditions preferred. Protecting groups are well known in the art, see for example Greene, T. W. Protective Groups in Organic Synthesis, John Wiley and Sons, Inc. New York, 1991.

Alternatively, (3R,3aS,6aR)-hexahydrofuro[2,3-b]furan-3-ol and precursors thereof may be obtained through a dynamic diastereoselective resolution of a racemate mixture of hexahydrofuro[2,3-b]furan-3-ol. In such a case, the racemate mixture is submitted to the action of certain enzymes such as porcine pancreatic lipase, candida cylindracca, pancreatin, and the like, in the presence of suitable solvents and reagents such as acetic anhydride, and vinyl acetate. This alternative route allows the in situ production of the desired (3R,3aS,6aR)-hexahydrofuro[2,3-b]furan-3-ol enantiomer, which can be conveniently activated in a one-pot procedure; the undesired stereoisomer is blocked or rendered inert.

Examples of coupling agents used in carbamoylation reactions are carbonates such as bis-(4-nitrophenyl)carbonate, disuccinimidyl carbonate (DSC), carbonyl diimidazole (CDI). Other coupling agents include chloroformates, such as p-nitrophenylchloroformate, phosgenes such as phosgene and triphosgene.

In particular, when the (3R,3aS,6aR)-hexahydrofuro[2,3-b]furan-3-ol is processed with disuccinimidyl carbonate, 1-([[[(3R,3aS,6aR)hexahydrofuro[2,3-b]furan-3-yloxy]carbonyl]oxy)-2,5-pyrrolidinedione is obtained. Said compound is a preferred (3R,3aS,6aR)-hexahydrofuro[2,3-b]furan-3-yl derivate.

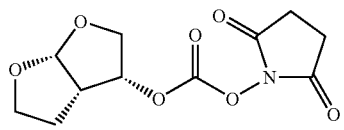

For the activation of the (3R,3 aS,6aR)-hexahydrofuro[2,3-b]furan-3-ol and precursors thereof with a coupling agent it is recommended that the alcohol is present at a concentration between 1% and 20% (w/w), preferably at a concentration between 2% and 15% (w/w), more preferably at a concentration between 4% and 10% (w/w).

Reaction of (3R,3aS,6aR)-hexahydrofuro[2,3-b]furan-3-yl derivate with compound of formula (5) will be performed in the presence of suitable solvents, such as tetrahydrofuran, dimethylformamide, acetonitrile, dioxane, dichloromethane or chloroform, and optionally with bases, such as triethylamine although further cominations from the solvents and bases hereinabove disclosed are also embodied. Among the solvents, preferred solvents are aprotic solvents such as tetrahydrofuran, acetonitrile, dimethylformamide, ethyl acetate, and the like.

In one embodiment, during the coupling of (3R,3aS,6aR)-hexahydrofuro[2,3-b]furan-3-yl derivate with compound of formula (5), said derivate is present at a concentration between 1% and 15% (w/w), preferably at a concentration between 5% and 12% (w/w), more preferably at a concentration between 8% and 12% (w/w).

Carbamoylation reaction is suitably carried out at a temperature between −70° and 40° C., preferably between −10° C. and 20° C.

The compound obtained from the coupling of (3R,3aS,6aR)-hexahydrofura[2,3-b]furan-3-yl derivate with compound of formula (5) is compound of formula (6). Compound of formula (6) will preferably be solvated with alcohols such as ethanol, methanol, being the ethanolate solvate form preferred. Solvation of compound of formula (6) is described in PCT/EP03/50176 (Tibotec N.V.), which is incorporated herein by reference.

(6)

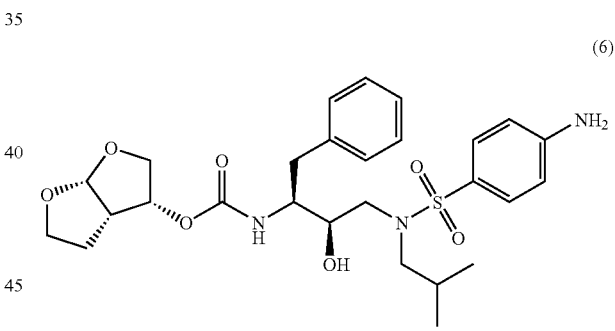

In each of the preparations presented above, the reaction products, for instance compounds of formula (3), (3'), (4), (4'), (5) and the end product compound of formula (6) may be isolated from the reaction medium and, if necessary, further purified according to methodologies generally known in the art such as, for example, extraction, crystallization, distillation, trituration and chromatography.

For therapeutic use, the salts of the compounds according to the invention, are those wherein the counter-ion is pharmaceutically or physiologically acceptable. However, salts having a pharmaceutically unacceptable counterion may also find use, for example, in the preparation or purification of a pharmaceutically acceptable compound of the present invention. All salts, whether pharmaceutically acceptable or not are included within the ambit of the present invention.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, phosphate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such a sarginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethylbromides and others. Other pharmaceutically acceptable salts include the sulfate salt ethanolate and sulfate salts.

The term "polymorphic form" refers to the properly of compounds of formula (5) and (6) to exist in amorphous form, in polymorphic form, in crystalline form with distinct structures varying in crystal hardness, shape and size. The different crystalline forms can be detected by crystallographic techniques or indirectly by assessment of differences in physical and/or chemical properties associated with each particular polymorph. The different polymorphs vary in physical properties such as solubilty, dissolution, solid-state stability as well as processing behaviour in terms of powder flow and compaction during tabletting.

The terms "pseudopolymorphic form" or "solvates" refer to aggregates that consists of molecules of compound of formula (6) and salts thereof, entrapped or complexed with solvent molecules, on a mol/mol basis and at various degrees of solvation.

The intermediates according to the invention may also exist in their tautomeric forms. Such forms, although not explicitly indicated in the compounds described herein, are intended to be included within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i. e. minimum 90% of one isomer and maximum 10% of the other possible isomers) up to a stereoisomeric excess of 100% (i. e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltaric acid and camphosulfonic acid. Alternatively, enantiomers may be separated by chromatographic techniques using chiral stationary phases. Said pure stereochemically isomeric forms may also be derived from the corresponding pure stereochemicaly isomeric forms of the appropriate starting materials, provided that the reaction occurs stereospecifically. Preferably, if a specific stereoisomer is desired, said compound will be synthesized by stereospecific processes. These processes will advantageously employ enantiomerically pure starting materials.

The diastereomeric racemates of the compounds and intermediates of this invention can be obtained separately by conventional methods. Appropriate physical separation methods which may advantageously be employed are, for example, selective crystallization and chromatography, e. g. column chromatography.

It is clear to a person skilled in the art that the compounds and intermediates of this invention contain at least two asymmetric centers and thus may exist as different stereoisomeric forms. These asymmetric centers are indicated with an asterisk (*) in the figures below.

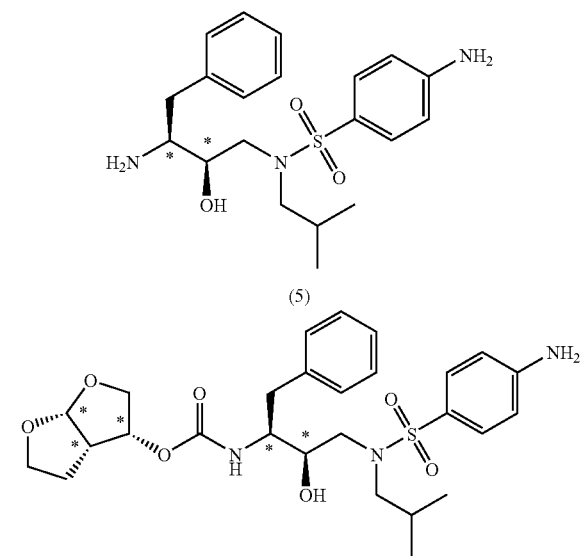

The absolute configuration of each asymmetric center that may be present in the compounds and intermediates of this invention may be indicated by the stereochemical descriptors R and S, this R and S notation corresponding to the rules described in Pure Appl. Chem. 1976, 45,11-30.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C13 and C-14.

The reagents and solvents used throughout the specification may be replaced by functional alternatives or functional derivatives thereof as they are known to a person skilled in the art. Also the reaction conditions such as stirring times, purification and temperature may be adjusted to optimise reaction conditions. Similarly, the reaction products may be isolated from the medium and, if necessary, further purified according to methodologies generally known in the art such as, for example, extraction, crystallization, trituration and chromatography. A number of intermediates and starting materials used in the foregoing preparations are known compounds, while others may be prepared according to methods known in the art of preparing said or similar compounds.

The compounds of formula (5) and all intermediates leading to the formation of stereoisomerically pure compounds are of particular interest in preparing 4-amino-benzene sulfonamide compounds, as HIV protease inhibitors, as disclosed in WO 95/06030, WO 96/22287, WO 96/28418, WO 96/28463, WO 96/28464, WO 96/28465 WO 97/18205, and WO 02/092595 all incorporated herein by reference, and in particular, the HIV-protease inhibitor compound of formula (6), and any addition salt, polymorphic and/or pseudopolymorphic forms thereof.

Thus, the present invention also relates to HIV protease inhibitors such as compound of formula (6) and any pharmaceutically acceptable salt, polymorphic or pseudopolymorphic form thereof, obtained by using any intermediate as described herein, wherein both, intermediates and compound of formula (6), are prepared as described in the present invention.

Thus, the present invention also relates to HIV protease inhibitors such as compound of formula (6) and any pharmaceutically acceptable salt, polymorphic or pseudopolymorphic form thereof, obtained by using a compound of formula (5) as intermediate, wherein both compound of formula (5) and compound of formula (6) are prepared as described in the present invention.

The following examples are meant to illustrate the present invention. The examples are presented to exemplify the invention and are not to be considered as limiting the scope of the invention.

EXAMPLES

Example 1

Preparation of (1-Benzyl-2-hydroxy-3-isobutylamino-propyl)-carbamic acid tert-butyl ester To 154.4 Kg isobutylamine, (1-Oxiranyl-2-phenyl-ethyl)-carbamic acid tert-butyl ester (53.3 Kg) was added, and then the solution was heated under reflux. Under reduced pressure, isobutylamine was removed from the reaction mixture, and then replaced by toluene.

Example 2

Preparation of (1-Benzyl-2-hydroxy-3-[isobutyl-(4-nitro-benzenesulfonyl)-amino]-propyl}-carbamic acid tert-butyl ester 26.7 kg triethylamine were added to the prepared solution in Example 1, and the obtained solution was heated to 82-88° C. To the solution, a solution of 4-nitrobenzene-sulfonyl chloride (53 Kg) in toluene was gradually added and stirred. The obtained reaction mixture was washed with water.

The washed solution of (1-Benzyl-2-hydroxy-3-[isobutyl-(4-nitro-benzenesulfonyl)-amino]-propyl)-carbamic acid tert-butyl ester was heated, then toluene and n-heptane were added. This solution was cooled and seeded with crystals of (1-Benzyl-2-hydroxy-3-[isobutyl-(4-nitro-benzenesulfonyl)-amino]-propyl)-carbamic acid tert-butyl ester. After the deposition of crystals was observed, the solution was kept stirring and then was slowly cooled to 20-30° C. The resulting crystals were filtered off and washed with a mixed solution composed of toluene and n-heptane to give the wet crystals of (1-Benzyl-2-hydroxy-3-[isobutyl-(4-nitro-benzenesulfonyl)-amino]-propyl)-carbamic acid tert-butyl ester (yield 87-91%, based on (1-Oxiranyl-2-phenyl-ethyl)-carbamic acid tert-butyl ester).

Example 3

Preparation of (1-Benzyl-2-hydroxy-3-[isobutyl-(4-amino-benzenesulfonyl)-amino]-propyl)-carbamic acid tert-butyl ester The wet crystals of (1-Benzyl-2-hydroxy-3-[isobutyl-(4-nitro-benzenesulfonyl)-amino]-propyl)-carbamic acid tert-butyl ester were suspended in ethanol (around 950 L), and then hydrogenated in the presence of 10 wt % palladium carbon at around 5-30° C. After the resulting reaction mixture was filtered to remove the palladium-carbon, the filtrate was concentrated under reduced pressure to give a solution of (1-Benzyl-2-hydroxy-3-[isobutyl-(4-amino-benzenesulfonyl)-amino]-propyl)-carbamic acid tert-butyl ester in ethanol.

Example 4

Preparation of 4-Amino-N-(2R,3S)(3-amino-2-hydroxy-4-phenyl-butyl)-N-isobutyl-benzenesulfonamide The solution of (1-Benzyl-2-hydroxy-3-[isobutyl-(4-amino-benzenesulfonyl)-amino]-propyl)-carbamic acid tert-butyl ester obtained in Example 3 was heated for reflux, and then concentrated hydrochloric acid (35-37 kg) was added. The solution was stirred.

The obtained solution was then cooled to 40±3° C. followed by the addition of water. Adjustment of the pH of the solution to around 9.5 with aqueous solution of sodium hydroxide gave crystals 4-Amino-N-(3-amino-2-hydroxy-4-phenyl-butyl)-N-isobutyl-benzenesulfonamide. Additional water was added to this solution to adjust the concentration of 4-Amino-N-(3-amino-2-hydroxy-4-phenyl-butyl)-N-isobutyl-benzenesulfonamide to 5.5-5.8 wt %, and then this solution was cooled to 6±4° C. The resulting crystals were filtered off and washed with a mixed solution composed of water and ethanol and then washed with water. The resulting wet crystals were subjected to vacuum drying to give the product of (2R,3S)-N-(3-amino-2-hydroxy-4-phenylbutyl)-N-isobutyl-4-amino-benzenesulfonamide. Yields were 75~85% based on (1-Benzyl-2-hydroxy-3-[isobutyl-(4-nitro-benzenesulfonyl)-amino]-propyl)-carbamic acid tert-butyl ester.

Example 5

Preparation of 4-Amino-N-((2R,3S)-3-amino-2-hydroxy-4-phenylbutyl)-N-(isobutyl)benzene sulfonamide 50,00 g of (1-Benzyl-2-hydroxy-3-[isobutyl-(4-nitro-benzenesulfonyl)-amino]-propyl)-carbamic acid tert-butyl ester, which was prepared according to the procedures described in WO99/48885, WO01/12599, and WO01/46120; 2 mol % of ethanolamine and palladium on activated charcoal were suspended in methanol, rendered inert and evacuated. At an inside temperature of 22-30° C. about 3,0 eq of hydrogen were added at overpressure. Then the catalyst was removed by filtration. The colorless (to slightly yellowish) solution was treated with 21.70 g hydrochloric acid 37% and heated to reflux for 2 h. After complete conversion methanol was removed by distillation. The precipitation was performed in a mixture of the solvents MeOH/Water/IPA-mixture 1:8:6,5. At a temperature of 0-7° C., sodium hydroxide 30% was dosed until a pH value of pH>12.5 was reached. After 4 to 48 h the white precipitate was filtered and washed with water and isopropanol. The wet product was dried in vacuum at 65° C. The process yielded 36,94 g of a white to yellowish powder.

Example 6

Preparation of 4-Amino-N-((2R,3S)-3-amino-2-hydroxy-4-phenylbutyl)-N-isobutyl)benzene sulfonamide 50,00 g of (1-Benzyl-2-hydroxy-3-[isobutyl-(4-nitro-benzenesulfonyl)-amino]-propyl)-carbamic acid tert-butyl ester, which was prepared according to the procedures described in WO99/48885, WO01/12599, and WO01/46120; and palladium on activated charcoal were suspended in ethanol, rendered inert and evacuated. At an inside temperature of 22-30° C. about 3,0 eq of hydrogen were added at overpressure. Then the catalyst was removed by filtration. After distillation of the alcohol (1-Benzyl-2-hydroxy-3-[isobutyl-(4-amino-benzenesulfonyl)-amino]-propyl)-carbamic acid tert-butyl ester remained as a colorless foam in a yield of 97%. (1-Benzyl-2-hydroxy-3-[isobutyl-(4-amino-benzenesulfonyl)-amino]-propyl)-carbamic acid tert-butyl ester was dissolved in methanol treated with 21.70 g hydrochloric acid 37% and heated to reflux for 2 h. After complete conversion most of the alcohol was removed by distillation. The hydrochloric salt of 4-Amino-N-((2R,3S)-3-amino-2-hydroxy-4-phenylbutyl)-N-isobutyl)benzene sulfonamide was precipitated by removing most of the alcohol by distillation and adding dichloromethane to the 40° C. warm solution. By stirring and cooling to room temperature the hydrochloric salt precipitated immediately. The precipitation of 4-Amino-N-((2R, 3S)-3-amino-2-hydroxy-4-phenylbutyl)-N-isobutyl)benzene sulfonamide was performed by dissolving the hydrochloric salt in a mixture of the solvents EtOH/water-mixture 1:1. At a temperature of 0-7° C., sodium hydroxide 30% was dosed until a pH value of pH>12.5 was reached. After 4 to 48 h the white precipitate was filtered and washed with water and dried in vacuum. The process yielded 33,78 g of a white to yellowish powder.

Example 7

Preparation of (3R,3aS,6aR)-hexahydrofuro[2,3-b]furan-3-yl (1S,2R)-3-[[(4-aminophenyl)sulfonyl](isobutyl)amino]-1-benzyl-2-hydroxypropylcarbamate ethanolate 100 mmol (3R,3aS,6aR)-hexahydrofuro[2,3-b]furan-3-ol in ethyl acetate were added onto 120 mmol of disuccimidyl-carbonate (95%) in acetonitrile. Following, a solution of 140 mmol triethylamine in ethylacetate was added and stirred. The mixture was cooled and treated with a suspension of 92 mmol of 4-Amino-N-((2R,3S)-3-amino-2-hydroxy-4-phenylbutyl)-N-(isobutyl)benzene sulfonamide in ethyl acetate. 20 mmol methylamine, 41% aqueous solution in ethanol were added and the mixture was warmed. The reaction was washed twice with 10% Na₂CO₃-solution and with water. Solvent was evaporated and ethanol was added. Another portion of solvent was distilled off. The temperature was kept around 40-45° C. and crystallization was initiated by seeding. After stirring the mixture was cooled, stirred for another 90 min stirred, cooled and again stirred for 60 min. The precipitate was filtered and washed with ethanol. The wet product was dried in vacuo at 40° C. 43.5 g of (3R,3aS,6aR)-hexahydrofuro[2,3-b]furan-3-yl (1S,2R)-3-[[(4-aminophenyl)sulfonyl](isobutyl) amino]-1-benzyl-2-hydroxypropylcarbamate were suspended in ethanol abs. and dissolved. The clear solution was cooled and seeding was applied. Crystallization occurred while cooling the mixture. Stirring was continued for another 60 min, followed by cooling, stirring and filtering off the product, which was washed with cold ethanol abs. The wet product was dried in vacuo at 40° C. Yield: 42.1 g=71%.

Example 8

Preparation of (3R,3aS,6aR)-hexahydrofuro[2,3-b]furan-3-yl (1S,2R)-3-[[(4-aminophenyl)sulfonyl](isobutyl)amino]-1-benzyl-2-hydroxypropylcarbamate ethanolate 100 mmol (3R,3aS,6aR)-hexahydrofuro[2,3-b]furan-3-ol in ethyl acetate were added onto 105 mmol of bis-(4-nitrophenyl)carbonate in acetonitrile. Following, a solution of 250 mmol triethylamine in ethylacetate was added and stirred. The mixture was treated with a suspension of 95 mmol of 4-Amino-N-(2R,3S)-3-amino-2-hydroxy-4-phenyl-butyl)-N-(isobutyl)benzene sulfonamide in ethyl acetate. 20 mmol methylamine, 41% aqueous solution in ethanol were added. The reaction was washed three times with 10% K₂CO₃-solution and with water. Solvent was evaporated and ethanol was added. Another portion of solvent was distilled off. The temperature was kept around 40-45° C. and crystallization was initiated by seeding. After stirring the mixture was cooled, stirred for another 90 min stirred, cooled and again stirred for 60 min. The precipitate was filtered and washed with ethanol. The wet product was dried in vacuo at 40° C. 43.5 g of (3R,3aS,6aR)-hexahydrofuro[2,3-b]furan-3-yl (1S,2R)-3-[[(4-aminophenyl) sulfonyl](isobutyl)amino]-1-benzyl-2-hydroxypropylcarbamate were suspended in ethanol abs. and dissolved. The clear solution was cooled and seeding was applied. Crystallization occurred while cooling the mixture. Stirring was continued for another 60 min, followed by cooling, stirring and filtering off the product, which was washed with cold ethanol abs. The wet product was dried in vacuo at 40° C. Yield: 47.9 g=81%.

Example 9

Preparation of (3R,3aS,6aR)-hexahydrofuro[2,3-b]furan-3-yl (1S,2R)-3-[[(4-aminophenyl)sulfonyl](isobutyl)amino]-1-benzyl-2-hydroxypropylcarbamate ethanolate 100 mmol (3R,3aS,6aR)-hexahydrofuro[2,3-b]furan-3-ol in acetonitrile were added onto 110 mmol of disuccimidyl-carbonate (95%) in acetonitrile. Following 300 mmol pyridine was added and stirred. The mixture was cooled and treated with a suspension of 95 mmol of 4-Amino-N-((2R, 3S)-3-amino-2-hydroxy-4-phenylbutyl)-N-(isobutyl)-benzene sulfonamide in acetonitrile, followed by 100 mmol of triethylamine. 20 mmol methylamine, 41% aqueous solution in water were added and the mixture was warmed. 80 g solvent were distilled off, MTBE was added and the reaction mixture was washed with 10% Na₂CO₃-solution, with a mixture of sodium sulfate in sulfuric acid and again with 10% Na₂CO₃-solution. Solvent was evaporated and ethanol was added. Another portion of solvent was distilled off. The temperature was kept around 40-45° C. and crystallization was initiated by seeding. After stirring the mixture was cooled, stirred for another 90 min stirred, cooled and again stirred for 60 min. The precipitate was filtered and washed with ethanol. The wet product was dried in vacuo at 40° C. 43.5 g of (3R,3aS,6aR)-hexahydrofuro[2,3-b]furan-3-yl (1S,2R)-3-[[(4-aminophenyl) sulfonyl](isobutyl)amino]-1-benzyl-2-hydroxypropylcarbamate were suspended in ethanol abs. and dissolved. The clear solution was cooled and seeding was applied. Crystallization occurred while cooling the mixture. Stirring was continued for another 60 min, followed by cooling, stirring and filtering off the product, which was washed with cold ethanol abs. The wet product was dried in vacuo at 40° C. Yield: 48.1 g=81%.

The invention claimed is:
1. A process for preparing compound of formula (6),

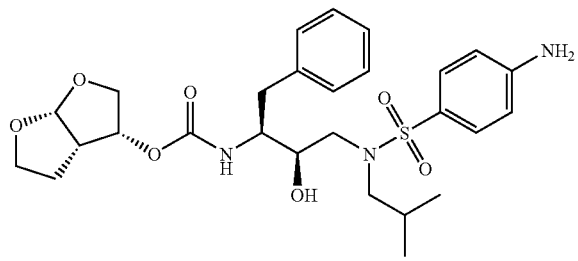

(6)

or an addition salt, thereof; comprising:
(i) introducing an isobutylamino group in compound of formula (1)

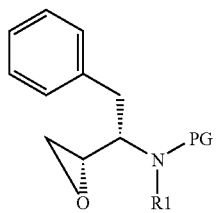

(1)

wherein
PG represents an amino-protecting group;
$R_1$ is hydrogen or $C_{1-6}$alkyl;
(ii) introducing a p-nitrophenylsulfonyl group in the resultant compound of step (i);
(iii) reducing the nitro moiety of the resultant compound of step (ii);
(iv) deprotecting the resultant compound of step (iii); and
(v) coupling the resultant compound of step (iv) with a (3R,3aS,6aR)-hexahydrofuro[2,3-b]furan-3-yl derivative.

2. A process according to claim 1 for preparing compound of formula (6), comprising the steps of:
(i) introducing an isobutylamino group in compound of formula (1');

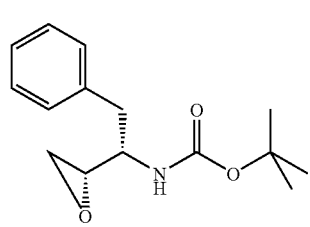

(1')

to obtain compound of formula (2');

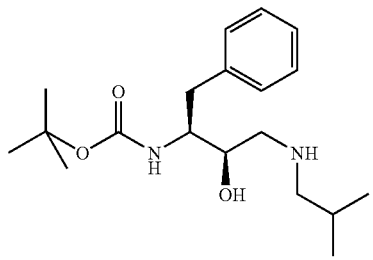

(2')

(ii) introducing a p-nitrophenylsulfonyl group into compound of formula (2') to obtain compound of formula (3');

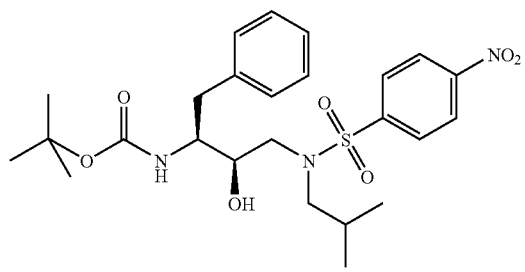

(3')

(iii) reducing the nitro moiety of compound of formula (3') to obtain compound of formula (4');

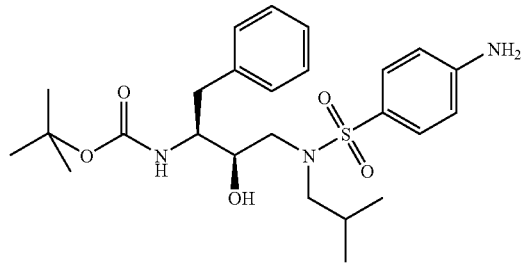

(4')

(iv) deprotecting compound of formula (4') to obtain compound of formula (5)

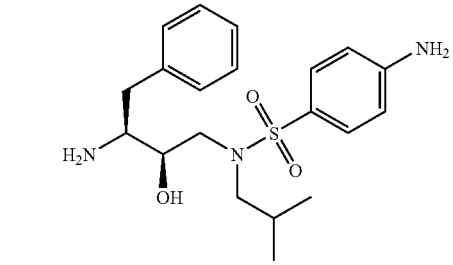

(5)

coupling compound of formula (5) with (3R,3aS,6aR)-hexahydrofuro[2,3-b]furan-3-yl derivative to obtain compound of formula (6).

3. A process according to claim 1 wherein step (i) is carried out in toluene.

4. A process according to claim 1 wherein step (ii) is carried out in toluene, ethylacetate, methylene chloride, dichloromethane, or tetrahydrofuran.

5. A process according to claim 1 wherein step (iii) is carried out in the presence of up to 10 mol % primary or secondary amine, with palladium on charcoal under a hydrogen atmosphere.

6. A process according to claim 1 wherein step (iv) is carried out in acidic or basic conditions.

7. A process according to claim 2 wherein compound of formula (5) is crystallized by dissolving in a solvent system, adjusting the pH to a value higher than 9 and keeping the concentration of compound of formula (5) in solution in a value between 4% and 15% (w/w).

8. A process according to claim 2 wherein compound of formula (5) is crystallized at a temperature between 0° C. and 10° C.

9. A process according to claim 7 wherein seed crystals of compound of formula (5) are added during crystallization.

10. A process according to claim 7 wherein the solvent system comprises one or more water-miscible solvents and water.

11. A process according to claim 7 wherein the solvent system comprises one or more water-immiscible solvents and water.

12. A process according to claim 10 wherein the solvent system is methanol, isopropanol, and water in a ratio 1:6.5:8 respectively.

13. A process according to claim 2 wherein (3R,3aS,6aR)-hexahydrofuro[2,3-b]furan-3-ol is reacted with bis-(4-nitrophenyl)carbonate before coupling to compound of formula (5).

14. A process according to claim 2 wherein (3R,3aS,6aR)-hexahydrofuro[2,3-b]furan-3-ol is reacted with disuccinimidyl carbonate before coupling to compound of formula (5).

15. A process according to claim 13 wherein the reaction of (3R,3aS,6aR)-hexahydrofuro[2,3-b]furan-3-ol and the carbonic acid derivative is activated by an (amine-) base.

16. A process according to claim 2 wherein step (i) is carried out in toluene.

17. The process according to claim 5 wherein the amine is ethanolamine.

18. The process according to claim 15 wherein the (amine-) base is triethylamine or pyridine.

* * * * *